US012605131B2

(12) United States Patent
Highnam et al.

(10) Patent No.: US 12,605,131 B2
(45) Date of Patent: Apr. 21, 2026

(54) SYSTEM AND METHOD FOR THE QUANTIFICATION OF CONTRAST AGENT

(71) Applicants: VOLPARA HEALTH TECHNOLOGIES LIMITED, Wellington (NZ); VOLPARA SOLUTIONS EUROPE LIMITED, Stockport (GB)

(72) Inventors: Ralph Highnam, Wellington (NZ); Melissa Hill, Issey les Moulineaux (FR)

(73) Assignee: LUNIT INTERNATIONAL LIMITED, Wellington (NZ)

( * ) Notice: Subject to any disclaimer, the term of this patent is extended or adjusted under 35 U.S.C. 154(b) by 321 days.

(21) Appl. No.: 18/013,514

(22) PCT Filed: Jul. 5, 2021

(86) PCT No.: PCT/IB2021/056019
§ 371 (c)(1),
(2) Date: Dec. 28, 2022

(87) PCT Pub. No.: WO2022/003656
PCT Pub. Date: Jan. 6, 2022

(65) Prior Publication Data
US 2023/0248327 A1 Aug. 10, 2023

(30) Foreign Application Priority Data
Jul. 3, 2020 (GB) ...................................... 2010219

(51) Int. Cl.
*A61B 6/00* (2024.01)
*A61B 6/50* (2024.01)
(Continued)

(52) U.S. Cl.
CPC .............. *A61B 6/481* (2013.01); *A61B 6/482* (2013.01); *A61B 6/502* (2013.01); *A61B 6/5282* (2013.01); *G16H 30/20* (2018.01); *G16H 30/40* (2018.01)

(58) Field of Classification Search
CPC ......... A61B 6/481; A61B 6/482; A61B 6/502; A61B 6/5282; A61B 6/5264;
(Continued)

(56) References Cited

U.S. PATENT DOCUMENTS

2008/0167552 A1* 7/2008 Bouchevreau ......... A61B 6/482
600/431
2010/0034348 A1* 2/2010 Yu ........................ A61B 6/4233
378/209
(Continued)

FOREIGN PATENT DOCUMENTS

WO 2020/059306 A1 3/2020

OTHER PUBLICATIONS

Chen, L., et al., "Impact of subtraction and reconstruction strategies on dual-energy contrast enhanced breast tomosynthesis with interleaved acquisition", Proceeding of Spine, vol. 8668, 2013, pp. 866850.
(Continued)

*Primary Examiner* — Kathleen Y Dulaney
(74) *Attorney, Agent, or Firm* — HOLLAND & HART LLP

(57) ABSTRACT

The present invention relates to contrast-enhanced radiographic imaging, the quantification of contrast agent in tissue and the assessment of the radiographic image quality. The invention provides a radiographic system-agnostic method to assess tissue administered with a radio-opaque contrast agent. The method is a system-agnostic means to accurately quantify contrast agent content in normal tissue
(Continued)

and in cancerous tissue from contrast-enhanced radiographic images, and to assess and verify image quality and the efficacy of a clinical assessment from these images.

11 Claims, 7 Drawing Sheets

(51) Int. Cl.
  *G16H 30/20* (2018.01)
  *G16H 30/40* (2018.01)
(58) Field of Classification Search
  CPC ....... A61B 6/5235; A61B 6/463; A61B 6/469; G16H 30/20; G16H 30/40
  USPC ............ 382/128, 130, 132; 600/431; 378/54
  See application file for complete search history.

(56) References Cited

U.S. PATENT DOCUMENTS

| | | | | |
|---|---|---|---|---|
| 2012/0068702 A1* | 3/2012 | Feiweier | .......... | G01R 33/56509 324/309 |
| 2015/0119706 A1* | 4/2015 | Lu | ....................... | A61K 49/0438 600/425 |
| 2016/0157806 A1* | 6/2016 | Han | ........................ | A61B 6/583 378/54 |
| 2016/0256126 A1* | 9/2016 | Wehnes | .................... | G06T 7/11 |
| 2016/0292851 A1* | 10/2016 | Hamauzu | .................. | G06T 5/70 |
| 2017/0061613 A1* | 3/2017 | Karczmar | ............ | G06T 7/0016 |
| 2017/0116730 A1* | 4/2017 | Yamanaka | ................ | G06T 5/94 |
| 2017/0251991 A1* | 9/2017 | Wang | .................... | A61B 6/502 |
| 2017/0316588 A1* | 11/2017 | Homann | ............... | G06T 11/008 |
| 2018/0174341 A1* | 6/2018 | Palma | .................... | A61B 8/463 |
| 2018/0240224 A1* | 8/2018 | Fukuda | ................ | G01B 15/025 |
| 2018/0333109 A1* | 11/2018 | Zamenhof | ............. | A61B 6/025 |
| 2019/0159741 A1* | 5/2019 | Fredenberg | ........... | A61B 6/484 |
| 2021/0145388 A1* | 5/2021 | Highnam | ................. | G06T 7/12 |
| 2023/0071400 A1* | 3/2023 | Abdolell | ............... | G16H 30/40 |

OTHER PUBLICATIONS

Han, S., et al., "A Quantification Method for Breast Tissue Thickness and Iodine Concentration Using Photon-Counting Detector", Journal of Digital Imaging, vol. 28, No. 5, 2015, pp. 594-603.

Huang, H., et al., "Comparison of contrast-enhanced digital mammography and contrast-enhanced digital breast tomosynthesis for lesion assessment", Journal of Medical Imaging, vol. 6, No. 3, 2019, 10 pages.

International Search Report and Written Opinion received for PCT Patent Application No. PCT/IB2021/056019, mailed on Nov. 11, 2021, 15 pages.

James, J. J. et al., "Contrast-enhanced spectral mammography (CESM)", Clinical Radiology, vol. 73, No. 8, 2018, pp. 715-723.

Karunamuni, R., et al., "Quantification of a silver contrast agent in dual-energy breast x-ray imaging", Proceedings of Spine, vol. 8668, 2013, pp. 866862.

Puong, S. et al., "Optimization of beam parameters and iodine quantification in dual-energy contrast enhanced digital breast tomosynthesis", Proceedings of Spine, vol. 6913, 2008, pp. 69130Z.

Savaridas, S. L. et al., "Could parenchymal enhancement on contrast-enhanced spectral mammography (CESM) represent a new breast cancer risk factor? Correlation with known radiology risk factors", Clinical Radiology, vol. 72, No. 12, 2017, 9 pages.

* cited by examiner

IODINE
CONCENTRATION
(mg/ml)
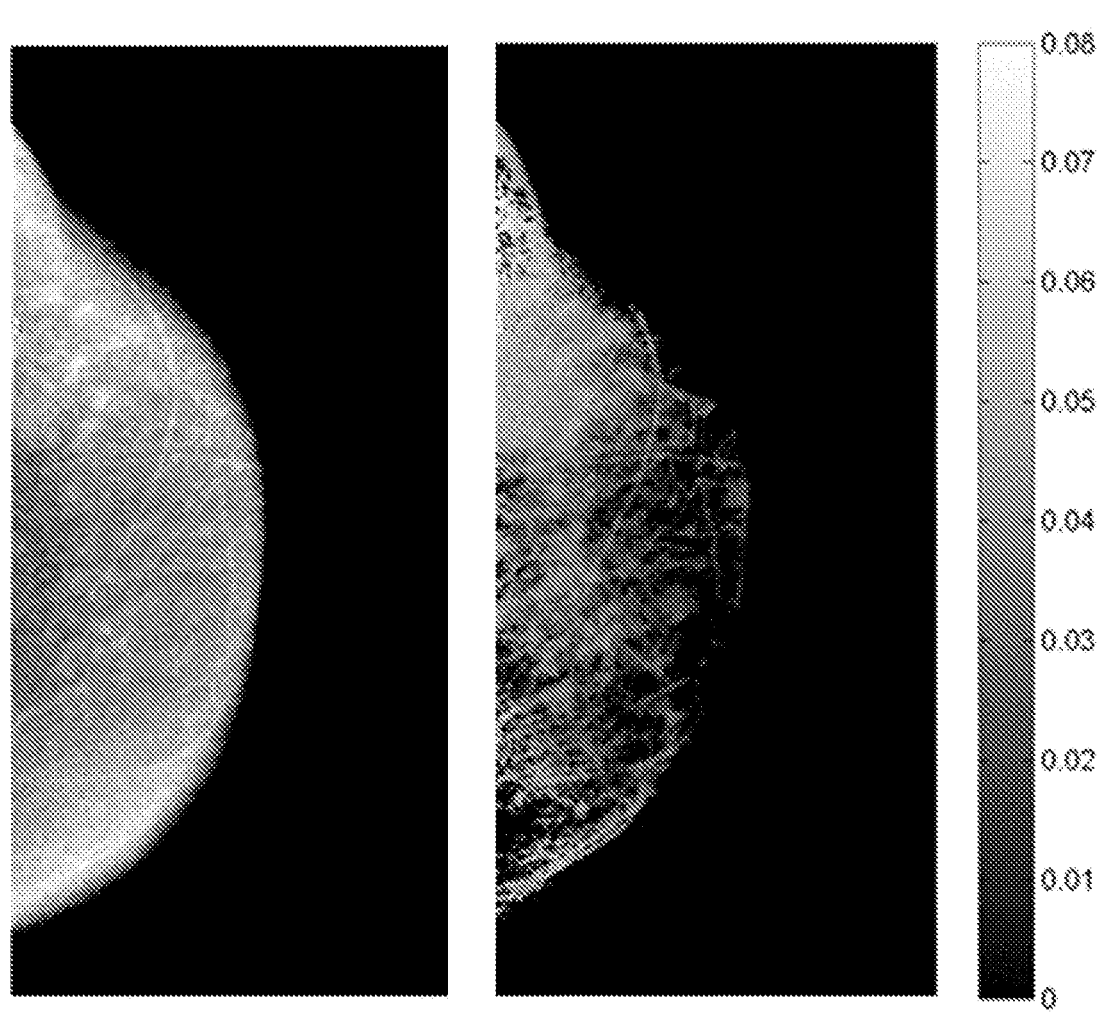
FIG. 2I                    FIG. 2J

SYSTEM AND METHOD FOR THE QUANTIFICATION OF CONTRAST AGENT

CROSS-REFERENCE TO RELATED APPLICATIONS

This is a national phase application of International Application No. PCT/IB2021/056019, filed 5 Jul. 2021, which claims the benefit of United Kingdom Patent Application No. 2010219.0, filed 3 Jul. 2020, the disclosures of which are incorporated herein, in their entireties, by this reference.

FIELD

The present invention relates to contrast-enhanced radiographic imaging, the quantification of contrast agent in tissue and the assessment of the radiographic image quality.

In particular, the present invention relates to system-agnostic means to accurately quantify contrast agent content in normal tissue and in cancerous tissue from contrast-enhanced radiographic images, and to assess and verify image quality and the efficacy of a clinical assessment from these images.

BACKGROUND

Contrast-enhanced (CE) radiographic imaging (RI) combines the use of a radiopaque contrast agent with a radiographic imaging technique. CE RI has been demonstrated with applications for breast cancer diagnosis in digital mammography (DM), computed tomography (CT), dedicated breast CT (bCT), and digital breast tomosynthesis (DBT), using a variety of detector technologies, including charge integrating detectors and photon-counting detectors. Most often an iodinated contrast agent is intravenously injected in CE RI. While these contrast agents are small enough to extravasate from normal vasculature, they provide an increased image contrast between tumour tissue and the surrounding normal tissue, based on differences in functional properties of tumour vessels that typically make them more porous to the contrast agent.

Among the benefits of CE RI are 1) the potential for functional information about the vasculature; 2) improved lesion conspicuity compared to non-contrast imaging; 3) quantitative diagnostic information; 4) concordant information to initial findings on non-contrast imaging; 5) better delineation of the extent of disease and identification of multifocality compared to non-contrast imaging; and 6) compared to breast MR, the relative speed, low-cost, and potential to serve as an alternative modality for contraindicated patients.

Improved lesion conspicuity, delineation of the extent of disease and identification of multifocality relate to a reduction in masking of a malignant lesion by radiopaque (known as 'dense') healthy fibroglandular tissue. The term 'masking' refers to the phenomenon whereby a lesion, in particular a malignant lesion, is inconspicuous to the human eye because it is surrounded by neighbouring or overlapping tissue of similar x-ray attenuation such that the image contrast is low in relation to the image contrast between normal tissues. In the case of a malignant lesion, this might constitute a 'missed cancer', and can have serious consequences for the subject. Mammography may generally be considered to have 'failed' where a cancer is missed.

Clinical indications for CE RI include diagnostic imaging, particularly for equivocal cases, screening of high-risk women, including women with dense breasts, and evaluation of response to therapy.

CE RI Imaging Technique

Two main approaches to CE RI have been investigated: single-energy (SE) subtraction (as described in Jong et al 'Contrast-enhanced digital mammography: initial clinical experience,' (2003), Diekmann et al in 'Digital mammography using iodine-based contrast media: initial clinical experience with dynamic contrast medium enhancement,' (2005) and Dromain et al 'Evaluation of tumor angiogenesis of breast carcinoma using contrast-enhanced digital mammography,' (2006)); and dual-energy (DE) decomposition (as described in Lewin et al 'Dual-energy contrast-enhanced digital subtraction mammography: feasibility,' (2003) and Dromain et al, 'Dual-energy contrast-enhanced digital mammography: initial clinical results,' (2011)).

Both SE and DE use intravenous administration of a radiographically opaque contrast agent to reveal functional information about the blood vessel characteristics and to improve lesion contrast compared to surrounding normal tissue. Injections are made at a dosage of about 1-1.5 ml/kg body weight via catheter into the antecubital vein contralateral to the breast of concern over a period of 30 to 60 s.

The problem of tissue superposition in conventional DM is mitigated in CE RI by the use of image subtraction. To take advantage of the relatively large x-ray attenuation difference between iodine and breast tissues beyond the iodine k-edge, the x-ray spectra used for SE CEDM imaging are shaped such that the mean x-ray energy lies above the iodine k-edge. The spectra used for sensitive iodine imaging, e.g. with tube potentials from 45 to 49 kV, are referred to as high-energy (HE) to distinguish them from conventional mammography spectra, which typically use tube potentials from 22 to 32 kV. Conventional mammography x-ray spectra are referred to here as low-energy (LE).

In DE CEDM, the LE and HE images are combined using methods to cancel the image contrast between fibroglandular tissue and adipose tissue and making regions of iodine uptake apparent against a comparatively uniform background (described in Lewin et al 'Dual-energy contrast-enhanced digital subtraction mammography: feasibility,' (2003), Puong et al 'Dual-energy contrast enhanced digital mammography using a new approach for breast tissue canceling,' (2007), Fredenberg et al 'Contrast-enhanced spectral mammography with a photon-counting detector,' (2010) and Arvanitis and Speller 'Quantitative contrast-enhanced mammography for contrast medium kinetics studies,' (2009)). One method for the DE image generation is a weighted subtraction, where a weighted proportion of the LE image, which mainly carries anatomical information, is subtracted from the HE image, which has a better visualisation of the contrast agent. The resulting subtracted DE image reveals areas of contrast agent uptake as being bright against a darker background where the signal from tissue with lower amounts of contrast agent uptake is largely cancelled out. These subtracted images are also referred to as 'recombined.'

In an ideal case, such as imaging with mono-energetic beams, no motion artefact, and no scattered radiation, the DE recombined image signal is linearly proportional to the amount of iodine. The LE and HE image pairs can be acquired rapidly (~1 s interval), or even simultaneously (as described in Fredenberg et al 'Contrast-enhanced spectral mammography with a photon-counting detector,' (2010) and Allec et al 'Single-layer and dual-layer contrast-enhanced mammography using amorphous selenium flat panel detectors,' (2011)) such that there may be minimal motion artefact present in the subtracted DE images. The presence of scattered radiation can be important in both quantitative and qualitative evaluations of DE decomposed images if not removed. For example, Arvanitis and Speller observed a 33% underestimation of projected iodine thickness without scatter correction applied.

An observed relationship between CE RI contrast-enhancement and blood vessel permeability has spurred interest in the quantification of contrast agent uptake. Contrast-enhancement is linked to the presence of a cancer, with both enhancement from the lesion itself being of diagnostic interest, and also that of the benign parenchyma, either adjacent to a lesion, or in a breast without disease. Benign parenchymal enhancement (BPE) was first observed in breast MRI, but has also been reported in CE DM exams, with good concordance between BPE observed in each modality. While the mechanism for contrast-enhancement in a lesion is relatively well understood based on the properties of tumour angiogenesis, BPE may not be directly indicative of disease. However, the degree of BPE has been shown to be linked to the risk of breast cancer and is believed to be related to the proliferative activity of the parenchyma. Conflicting reports exist as to the potential for a masking effect of BPE for lesion detection in CE exams.

Visual breast tissue assessment protocols, such the American College of Radiology Breast Imaging Reporting and Data Systems (BI-RADS®) 5th Edition, classify BPE on breast MRI as 'minimal' (less than 25% glandular tissue demonstrating enhancement), 'mild' (25%-50% glandular tissue demonstrating enhancement), 'moderate' (50%-75% glandular tissue demonstrating enhancement) or 'marked' (more than 75% glandular tissue demonstrating enhancement). The same classifications have generally been applied to CE DM.

Quantitative CE RI Analysis

Although CE RI has been demonstrated to have good performance when interpreted subjectively, it is also recognised that more diagnostic information is available than is currently being used via quantitative evaluation. In particular, it would be of value to objectively measure contrast agent tissue uptake for diagnostic purposes and to quantify and/or classify BPE for risk prediction. And for use in both normal and pathological tissue assessment, it is desirable to have information on the spatial correlation between contrast agent uptake and the local breast tissue composition. However, there are multiple factors that make quantitative analysis of CE RI images challenging that have not yet been overcome in prior art.

First, most clinical implementations of CE RI do not use true tomographic imaging techniques (e.g., CT and bCT), wherein the reconstructed voxel values nominally relate linearly to the underlying material composition, but instead are acquired as two-dimensional projections (e.g., DM), or use quasi-3D reconstruction (e.g., DBT), and as such have some degree of signal superposition that can impede quantification. For example, a method for extraction of the BPE using tissue segmentation has been proposed for breast MRI, which could be translated to CT and bCT, but this approach would not be suitable for analysis of images with signal superposition.

Several approaches to contrast quantification in CE DM and CE DBT rely on imaging a reference object, either for signal calibration at routine intervals, or with the object placed within the field-of-view of the clinical image. These approaches are system-specific and can be laborious, especially when calibration is required on a routine basis. Most work related to quantification in CE DM and CE DBT has also focused on contrast agent quantification in the lesion alone, and is often not applicable to normal tissue analysis.

For example, methods are known which suggest taking a differential signal measure between surrounding normal tissue and the lesion. However, in such method, no independent estimate of the normal tissue contrast agent content is available.

Furthermore, these methods do not address the second main challenge towards CE RI contrast quantification, which is CE RI image quality. Image artefacts are particularly deleterious and common features in CE RI. The artefacts can vary in presentation, especially as they can be specific to the image processing algorithm, but all either introduce 'dark' or 'bright' regions whose source of image signal variation is not strictly related to the presence or absence of contrast agent in the tissues. One example of image artefact in CE RI arises due to patient motion between, or during, successive image acquisitions. In this case an image recombination will typically have alternating bright and dark regions, especially around highly attenuating objects such as microcalcifications, markers or clips, and incomplete tissue cancellation in areas of soft tissue alone. These artefacts are visually distracting and can limit the diagnostic value of the images when the artefacts 'mask' lesion enhancement, leading to false negatives and poor sensitivity and/or mimic lesion enhancement, leading to false positives, which could also mean unnecessary biopsies, and poor specificity. In addition, these image artefacts limit the potential for signal quantification.

Other CE RI image quality factors include the breast positioning, breast compression and LE and HE image contrast and noise. Evaluation of breast positioning can indicate factors that are relevant to CE RI interpretation such as the potential for tissue that was missing from view, which would increase the uncertainty in the quantitative results. In addition to the importance of adequate breast compression to immobilise the breast and to avoid artefacts from uneven compression (e.g., air pockets) that also affect conventional mammography, breast compression has an additional influence on CE RI image quality in that the compression will influence blood flow, and thereby contrast agent perfusion in the breast. Compression that is too great may restrict blood flow and, thus, limit contrast agent uptake, and thereby the diagnostic value of CE RI. Poor LE and/or HE image contrast, or high noise are likely to correlate with poorer DE image conspicuity and thus, greater uncertainty in contrast uptake quantification, and might suggest that the image acquisition parameters could be optimised.

Advantageously, the present invention solves the problems left by the prior art of volumetric quantification of contrast agent by incorporating a model of image formation physics for calculating the attenuation properties of the constituent tissues of the breast from the acquired x-ray image based on the $h_{int}$ representation disclosed in PCT/GB2010/001472, and the standard attenuation rate (SAR) described in PCT/GB2010/001758. These give a volumetric measure of the tissue type/radiodensity at each pixel of a mammographic image, for the column of tissue between the detector element and the tube focal spot. This also standardises the image to describe only the tissue, and thus normalises the effect of the x-ray beam and image detector.

More specifically, the method described in PCT/GB2010/001758 estimates the x-ray attenuation of a lesion, in-vivo, from the mammographic image via the following steps:

(1) segmentation of the lesion in the mammographic image to ascertain: a prediction of the size of the lesion in the direction of the x-ray beam; the radiodensity of the background in the immediate vicinity of the lesion;

(2) building a model of the breast using the measured background radiodensity, the compressed breast thickness, and the lesion size from the segmentation, for forward simulation of the mammographic image using the model of image formation;

(3) ascertaining the lesion radiodensity using numerical optimisation to vary the lesion radiodensity in the simulation such that the difference in pixel intensity of the lesion in the simulated mammographic image and that observed in the acquired mammographic image is minimised.

According to the present invention, the above model-based methods for normal tissue and lesion tissue quantification are extended to include provision for contrast agent uptake into these tissues and means are provided to quantify the contrast agent itself and its effect on the normal tissue image appearance, which is typically subjectively classified (i.e., BPE).

Advantageously, the present invention incorporates means to assess image quality described in PCT/162017/054382, whereby measures relating to the position of the breast during an x-ray procedure are used to determine the adequacy of tissue demonstrated in the image, and to make an estimate of the presence of patient motion in the image. For example, detection of patient motion is used as means to: 1) estimate the image quality; 2) estimate the level of uncertainty in quantitative measurements of contrast agent uptake; 3) indicate the need for motion compensation and/or indicate appropriate image corrections that may be used to reprocess the contrast-enhanced image with superior image quality; and 4) trigger an indication of the need for optimised breast compression, which may include repositioning, during the examination.

Furthermore, the present invention provides a system-agnostic method to accurately quantify contrast agent content in normal tissue and in cancerous tissue from contrast-enhanced radiographic images, without a requirement of system calibration, and a method to assess image quality of these images as the quality relates both to efficacy of clinical assessment and confidence in the quantitative measurements.

In addition, the present invention can be used to identify BPE and to quantify BPE both in terms of contrast agent content, and in terms of the amount of tissue that preferentially takes up the contrast agent, referred to here as 'active' parenchyma, in a greater proportion relative to 'non-active' parenchyma. In both cases the image quality of the recombined view is evaluated such that the potential presence of image artefacts can be used to: 1) indicate the need for image correction(s) to accurately calculate the level of contrast agent, and report a confidence in the accuracy of the contrast agent quantification; and 2) make an estimate of the potential for lesion masking in these images.

SUMMARY OF THE INVENTION

According to an aspect of the invention there is a method to assess the uptake of a radio-opaque contrast agent in organ tissue(s) wherein low energy (LE) and high energy (HE) radiographic images (RI) of the organ tissue(s) are used to quantify the radio-opaque contrast agent content in the organ tissue(s).

The low energy (LE) and high energy (HE) radiographic images (RI) of the organ tissue may be x-ray scatter-corrected. They may be contrast enhanced (CE) RI wherein the organ tissue is subject to the radio-opaque contrast agent.

The method may facilitate assessment of organ tissue comprising non-active tissue and active tissue which has an additional concentration of a contrast agent compared to the non-active tissue. The organ tissue may comprise interesting tissue which includes the active tissue and a portion of the non-active tissue, and adipose tissue which includes a another portion of the non-active tissue and excludes all active tissue. The interesting tissue may include fibroglandular tissue and any lesions of the organ tissue. The interesting tissue and/or lesions may include one or more tumours.

The method may include correlating the additional contrast agent concentration in interesting tissue, but excluding lesions, with benign parenchymal enhancement to determine an objective measure of benign parenchymal enhancement that may be continuous, or categorised into two or more descriptive classifications. The method may included assessment of CE RI image quality wherein an estimate of the uncertainty in the quantification of the additional contrast agent concentration in interesting tissue is made and incorporated in a CE RI specific quality measure.

The LE RI and/or the HE RI may be used to produce at least one thickness map, at least one segmentation map, and at least one volumetric composition map of the organ tissue. Preferably the LE RI is used to produce the segmentation map.

The method may include adopting a relation that the concentration of the contrast agent in the non-active tissue is less that that of the concentration of contrast agent in active-tissue. This relation may be applied to the HE RI in particular, for example to use non-active fatty reference pixel values $g_{fat\_CA\_HE}$ and/or image pixel values for the $g_{CA_{HE}}(x,y)$ HE RI. This relation may be used advantageously to determine an additional contrast agent concentration in interesting tissue $\Delta C_{int}(x,y)$.

The method may include adopting a relation. that all the additional concentration of contrast agent occurs only in the interesting material.

A map in visual form may be produced of the additional contrast agent concentration in interesting tissue according to location in the CE RI.

The method may include adopting a relation that the total concentration of contrast agent in the active tissue is approximated as the sum of the concentration of the contrast agent in the non-active tissue plus an additional concentration of the contrast agent in the interesting tissue according to location in the RI.

The method may include producing the thickness map(s) of the organ includes using the LE RI. The thickness map may be used to determine a volumetric composition map. The thickness map may be an 'interesting tissue' thickness map, otherwise known as a density map. It is advantageous that, despite presence of contrast agent in the tissue in CE RI, knowledge of the non-active contrast agent concentration is not required to produce the interesting tissue thickness $h_{int}(x,y)$. The method may include determining the thickness of the interesting tissue by an approximation that in the LE RI there is no difference between the concentration of contrast agent in the active tissue versus in the non-active tissue.

The method may include adopting a relation that the additional concentration of the contrast agent in the interesting tissue according to location in the RI is zero.

The method may include adopting a relation that the thickness of the interesting tissue increases as the logarithm of a reference fat pixel value. The relation may include that the thickness of the interesting tissue decreases as the logarithm of the pixel values of the LE RI according to location in the LE RI. The relation may include that the thickness of the interesting tissue is inversely proportional to the difference between the linear attenuation coefficients of the interesting tissue and the fatty tissue of the LE RI. The reference fat pixel value may be determined from the LE RI without knowledge of the HE RI.

The method may include determining the additional contrast agent concentration in interesting tissue from a non-active fatty reference pixel value found from the HE image $g_{fat\_CA\_HE}$. The non-active fatty reference pixel value may be the same at all locations (x,y) of the image. Thus it may be said to be invariant of location since it does not vary with location.

The method may include determining the amount of interesting tissue, $h_{int}$ (x,y), by adopting a relation wherein the amount of interesting tissue, $h_{int}$ (x,y), is assumed to be identical in the LE RI and HE RI.

The method may include adopting a relation that the additional contrast agent concentration in interesting tissue $\Delta C_{int}$(x,y) may be determined from the HE RI and the LE RI. The relation to quantify the the additional contrast agent concentration in interesting tissue $\Delta C_{int}$(x,y) may be limited to where interesting tissue has a thickness greater than zero $h_{int}$ (x,y)>0.

The method may include adopting a relation that the additional contrast agent concentration in interesting tissue $\Delta C_{int}$(x,y) may be determined from a relation including the non-active fatty reference pixel values in the HE RI $g_{CA\_HE}$ (x,y).

According to another aspect of the invention image corrections are made to the raw LE and/or HE images according to image quality assessment and are used to produce a raw DE image, wherein the weighting factor is determined from a first difference between the linear attenuation coefficient of the interesting tissue and the adipose tissue in the HE RI, and a second difference between the linear attenuation coefficient of the interesting tissue and the adipose tissue in the LE RI and determining the ratio of the first difference to the second difference.

The present invention provides a system-agnostic method to accurately quantify contrast agent content in normal tissue and in cancerous tissue from contrast-enhanced radiographic images, without a requirement of system calibration. The present invention further provides a method to assess image quality of these images as it relates to efficacy of clinical assessment and as the quality affects the confidence level in the quantitative measurements or qualitative visualisation. The indication of inadequate image quality is further used to inform appropriate image corrections.

In addition, the present invention can be used to identify BPE and to quantify BPE both in terms of contrast agent content, and in terms of the amount of active parenchyma in a relative and/or greater proportion than non-active parenchyma. In both cases the image quality of the recombined view is evaluated such that the potential presence of image artefacts can be used to: 1) indicate the need for image correction(s) to accurately calculate the level of BPE, and to report a confidence in the accuracy of the BPE quantification; and 2) make an estimate of the potential for masking in these images.

Further advantages of the novel method include use of both vendor-generated DE images and generation of optimised 'raw' DE images. The method may use x-ray scatter correction, incorporation of patient specific breast density measurements and artefact reduction based on image registration informed by the detection of patient motion, provision of confidence level in contrast agent quantification and assessment of eth DE image artefacts and masking.

According to an embodiment contrast agent content may be quantified according to the following steps that account for breast composition, positioning, compression and image quality: Various combinations of some or all the steps may be used.

(1) the contrast agent in normal breast tissue(s) may be quantified using the method described in PCT/GB2010/001472 to calculate volume of dense tissue plus an estimation of contrast agent;

(2) quantification from step (1) may be used as an 'active tissue' or BPE quantity score and/or classification;

(3) image quality may be evaluated in the CE RI projections (LE, HE and DE), including image quality elements such as image noise, image contrast, x-ray scatter, breast compression, breast positioning, and motion blur;

(4) the measures from step (3) may be used to estimate the potential for masking/artefacts in CERI study views, to indicate the need for image correction(s) to improve the accuracy of contrast agent quantification and to determine a confidence level in the contrast agent and BPE quantification;

(5) unprocessed images may be corrected for deficiencies identified in step (4) and are used to produce 'raw' contrast-enhanced (e.g., DE) images with reduced artefacts and greater accuracy for BPE and contrast agent quantification.

According to another aspect of the invention there is method for assessing organ tissue comprising non-active tissue and active tissue, the active tissue has an increased concentration of a contrast agent compared to the non-active tissue. The method may comprise steps of: exposing the non-active tissue and the active tissue with x-ray to obtain scatter-corrected, contrast enhanced (CE) low energy (LE) radiation image and a scatter-corrected contrast enhanced (CE) high energy (HE) radiographic image (RI) of the organ tissue. It may include using the LE RI and/or the HE RI to produce at least one thickness map and at least one segmentation map and at least one volumetric composition map of the organ. The method may include deriving from at least one of the maps a quantified radio-opaque contrast agent content to clarify and/or distinguish the active tissue from the non-active tissue.

According to another aspect the invention there is a system arranged to implement the method disclosed herein, the system including: an image input device to input image pixel values and corresponding locations in at least one LE RI and at least one HE RI; a data input device LE and HE imaging system and contrast agent data; a map producing device to produce a segmentation map, an organ thickness map, a scatter corrected LE and HE maps, and a volumetric organ density map; and a contrast agent uptake assessment subunit to quantify radio-opaque contrast content in the organ tissue.

Further disclosure of the invention is included in the claims. The invention is further explained, by way of examples only, by the following description, to be read in conjunction with the appended drawings, in which:

BRIEF DESCRIPTION OF THE FIGURES

FIG. 2I is a raw dual-energy image; and

FIG. 2J is additional contrast agent concentration in the interesting tissue map of the additional contrast agent concentration in the interesting tissue $\Delta C_{int}(x,y)$, relative to concentration of contrast agent in non-active tissue so as to visually localize and quantify contrast agent uptake;

DETAILED DESCRIPTION

By way of illustrative embodiment, prior to contrast agent quantification multiple pre-processing steps are performed to maximize the measurement accuracy.

System and Method Inputs

The system and method inputs are CE RI exam images and their image metadata. Unprocessed ("raw," 'For Processing'), or processed ('For Presentation') CE RI images, or both, may be assessed. In a preferred embodiment quantification of contrast agent content and generation of a 'raw' contrast-enhanced, or raw DE, image is made using the unprocessed images.

The quantification method is demonstrated in FIG. 2 by way of the left craniocaudal view from a CE DM examination. Low-energy (LE: 28 kVp, W/Rh) energy mammograms are shown in FIG. 2A and FIG. 2B. In FIG. 2A a fold of tissue is visible at the edge and over the nipple can be seen compared to FIG. 2B. This tissue at the edge corresponds to the segmented region at the edge shown in FIG. 2D.

Figure 2A:
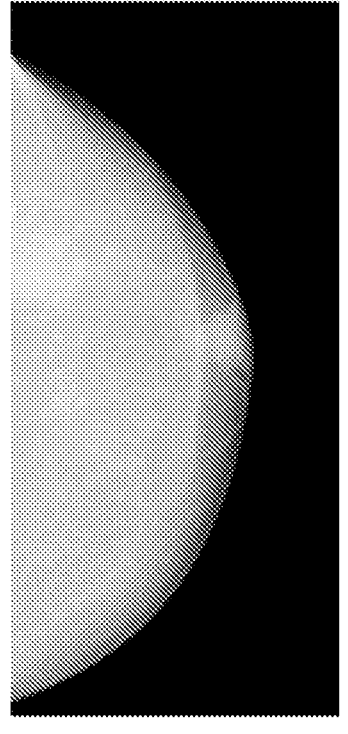
FIG. 2A is a first low-energy (LE) radiographic image (RI)
Figure 2B:
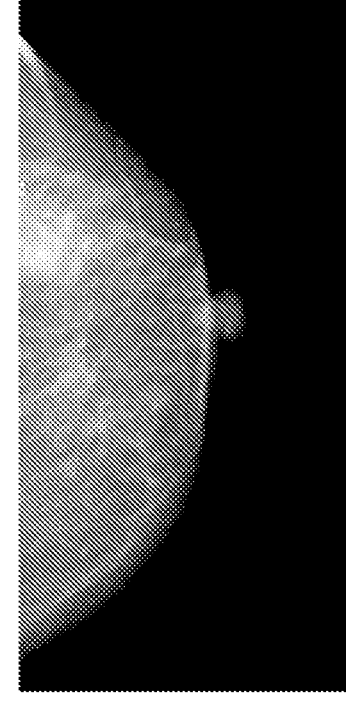
FIG. 2B is a second low-energy (LE) radiographic image (RI)
Figure 2C:
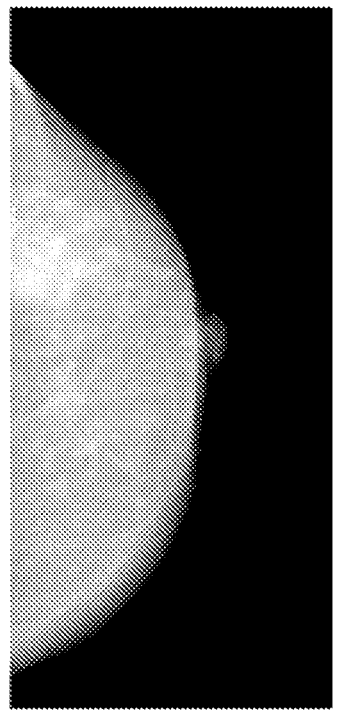
FIG. 2C is a high-energy (HE radiograph image (RI)

A high-energy (HE: 45 kVp, W/Cu) mammograms, shown in FIG. 2C. The LE and HE mammographs shown in FIGS. 2B and 2C respectively were acquired in rapid succession under a single breast compression 4 minutes after intravenous iodinated contrast agent administration. Other anatomical views, such as the mediolateral oblique view are typically acquired and can also be analyzed using the same methods.

In an embodiment, each of the CE RI images (e.g., LE, HE and DE) are analysed for the presence of motion artefact, such as using the methods described in PCT/162017/054382 except that the current approach is novel for taking into consideration requirements for using the LE and HE together. If substantial motion is found in the recombined image (e.g., DE), but with minimal or no motion in the source images (e.g., LE and HE), then motion compensation is applied, such as in the form of image registration between the source images. If one of the source images is found to contain motion artefact, then this image may be the image selected for transformation in the image registration process, while the sharper image will be used as a reference. If both source images are found to contain substantial motion artefact, then the step of motion compensation may be omitted on the basis that it is unlikely to improve either image quality or quantitative analysis. The following steps of analysis can be performed on either the images after motion compensation has been applied, or the original images, or both, which advantageously allows comparative analysis that can be used to determine uncertainty of interpretation from the uncorrected clinical images.

Image segmentation maps are generated for each anatomical view (i.e., CC & MLO) for each breast (right and left) using methods known to those skilled in the art, that identify breast tissue, muscle, and image background, for example the Otsu method or machine-learned segmentation. Estimation of the breast area in contact with the compression plates will be made. A model of breast thickness in the peripheral region that is not in contact with the compression plates will be applied to estimate the remaining breast tissue thickness as in PCT/162017/054382 except that the current approach is novel for taking into consideration requirements for using the LE and HE together. It is a preferred embodiment that the image segmentation map is produced from the raw LE image as this image type has the greatest contrast between breast image features.

Using the image segmentation map and image metadata that describes the acquisition conditions as an input, a breast thickness map is produced. The breast thickness map is an estimate of the total thickness of breast tissue at each image location (x,y). The breast thickness may be produced by methods known to those skilled in the art, including by applying the methods of PCT/TB2018/058663, where the accuracy of image parameters will be assessed to determine a best estimate of the breast thickness.

Figure 2D:
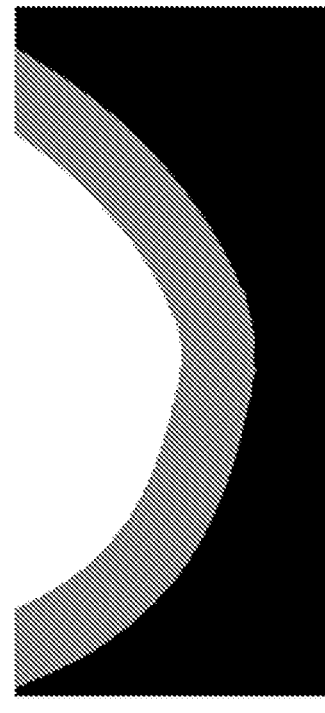
FIG. 2D is an illustration of an intermediate step segmentation.
Figures 2E, 2F:
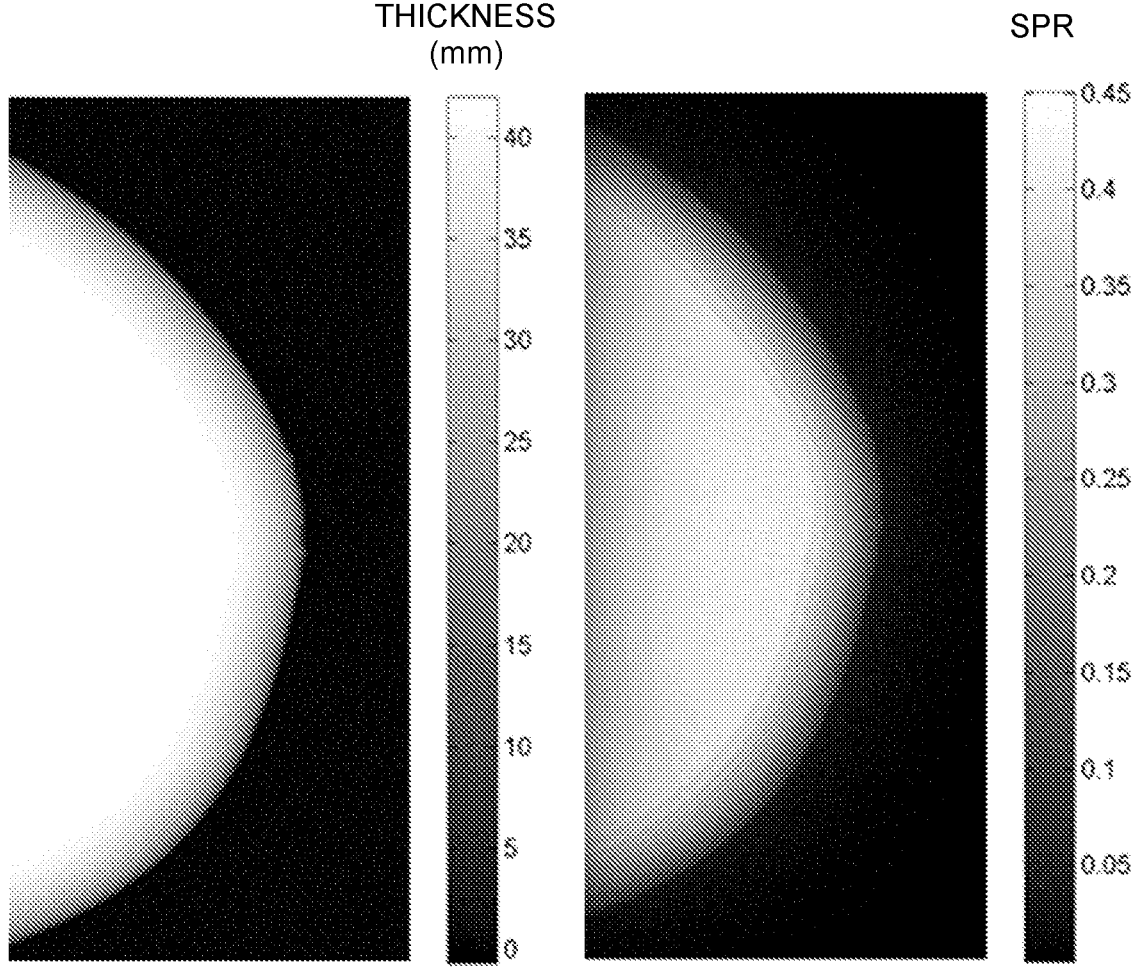
FIG. 2E is an illustration of an intermediate step of breast thickness estimate.
FIG. 2F is an illustration of an intermediate step of x-ray scatter-to-primary ratio (SPR) estimation in a LE image.

FIG. 2D shows an example segmentation of the unprocessed LE image in FIG. 2(a), which delineates an inner breast region in contact with the breast support and compression paddle (white) and a peripheral breast area (grey), where the thickness varies. The breast thickness map produced from these inputs is shown in FIG. 2E.

Using their associated segmentation and thickness maps, one or more mammographic images are transformed to a volumetric tissue composition map (e.g., by the Volpara density algorithm, or similar method). The set of images will include CE RI study images, but can also include prior conventional (non-contrast) images of the same subject, if available. The validity of, and uncertainty in, the CE RI-derived tissue composition data can be estimated through comparison with the tissue composition data derived from conventional images.

Integral to the derivation of the volumetric tissue composition map, but also for the generation of accurate DE subtracted images is accurate modelling of the image acquisition process. To develop this model, quantitative descriptive measurements are made from the mammographic images. This includes signal level measurements in one or more image regions. Reference descriptive image and subject data is also extracted from the image DICOM header, acquisition machine, or other database, which may include prior physical measurements or benchmark data. These data include x-ray spectrum information (anode/filter physical properties, kVp, mAs, exposure time, half-value layer, tube output), detector properties (including, but not limited to, detector conversion layer physical properties, detector element size, pixel size, pixel binning, detector pixel offset level, calibration status, number of image rows and columns); acquisition system characteristics (including, but not limited to, anti-scatter grid physical properties and performance characteristics; compression plate physical properties, detector cover physical properties, source-to-detector distance, breast support plate to detector distance; examination related data (including, but not limited to, compressed breast thickness, compression force, compression paddle tilt, contrast agent type and composition, method of contrast agent administration, injection rate, amount of contrast agent administered, start time of injection, image acquisition time).

In combination with the breast thickness map, these descriptive measurements are used to estimate the x-ray scatter field in each image. Any scatter estimation methods known to those skilled in the art may be applied, such as Monte Carlo modelling, machine-learned scatter models, and convolution with pre-computed scatter point-spread functions. In a preferred embodiment, pre-computed scatter point spread functions, as derived from Monte-Carlo simulations across a clinically relevant range of x-ray beam energies, breast tissue thicknesses and breast compositions, are convolved with the breast thickness map. The resulting scatter estimate is used to correct the image from which it was derived, and is repeated independently for each study image since the image acquisition parameters will differ between the images. For CE RI, a scatter-corrected LE and HE image are separately produced.

Figures 2G, 2H:
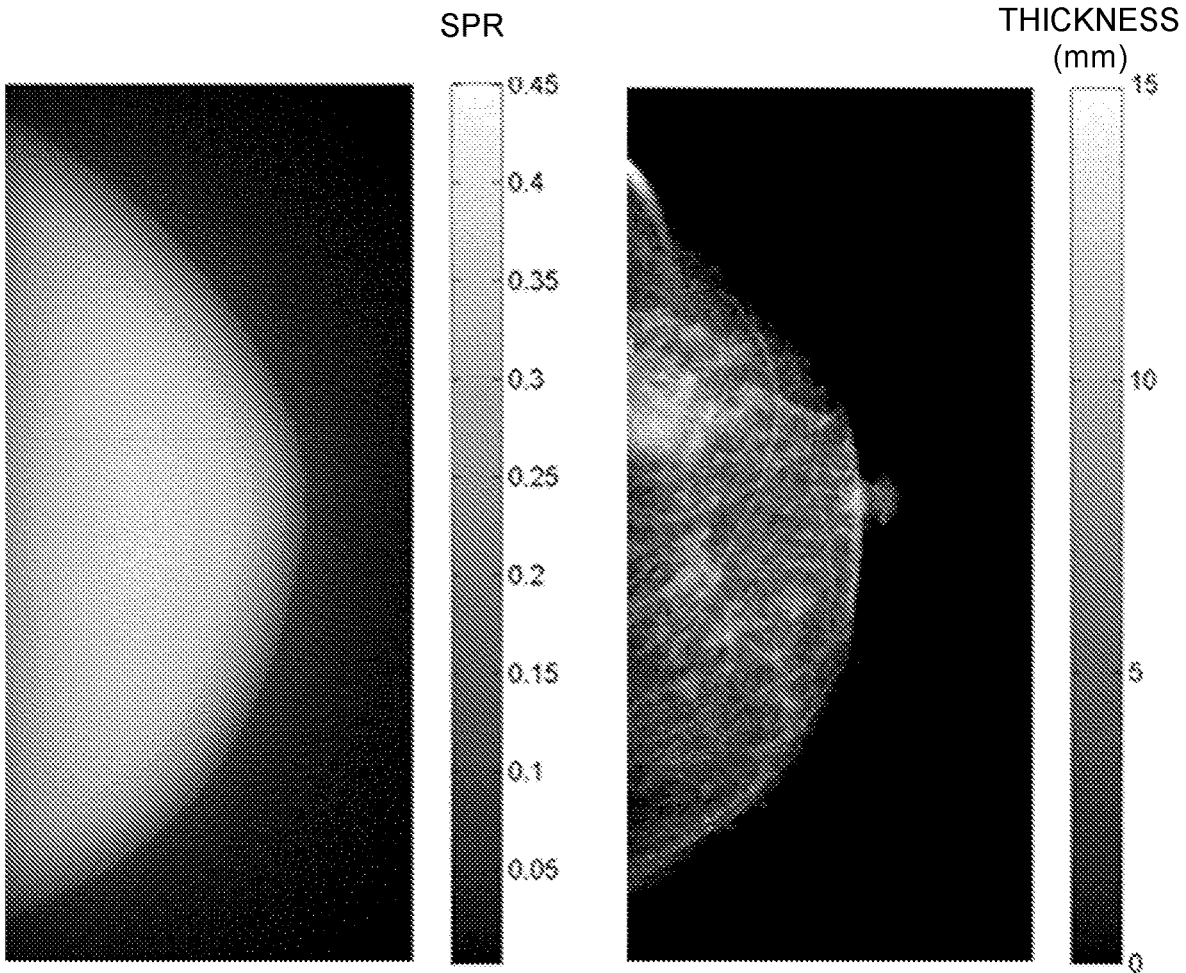
FIG. 2G is an illustration of an intermediate step of x-ray scatter-to-primary ratio (SPR) estimation in a HE image.
FIG. 2H is an 'interesting tissue' thickness map of the "interesting tissue" thickness $h_{int}(x,y)$.

FIG. 2F demonstrates the estimated scatter-to-primary ratio (SPR) without an anti-scatter grid for the LE image. FIG. 2G shows the SPR for the HE image, also without an anti-scatter grid.

The scatter-corrected CE RI images, with or without motion correction applied, together with the thickness maps, segmentation maps, and volumetric breast composition maps are input to a model for contrast agent content analysis.

In an embodiment, the model is as follows. In a conventional mammogram (where there is no contrast agent in tissue), image pixel values, $g(x,y)$, (after corrections for image offsets, x-ray scatter, and absorbed energy at the detector) are described by:

$$g(x,y)=\lambda e^{-H\mu_f}e^{-h_{int}(x,y)[\mu_{int}-\mu_f]},$$

and;

$$g(x,y)=g_{fat}e^{-h_{int}(x,y)[\mu_{int}-\mu_f]},$$

where H represents the compressed breast thickness, $h_{int}$ (x,y) is the thickness of 'interesting' tissue (fibroglandular tissue and any lesions), A accounts for the detected x-ray signal, and $\mu_{int}$ and $\mu_f$ represent the linear attenuation coefficients of interesting and fatty tissues, respectively.

Points are located in the mammographic image to estimate a reference fat pixel value, $g_{fat}$, as described in PCT/GB2010/001472:

$$g_{fat}=\lambda e^{-H\mu_f}$$

Under nominal conditions, it is assumed in CE RI that the contrast agent concentration is effectively equal in non-active adipose tissue and non-active fibroglandular tissue.

But, in metabolically active tissue the total contrast agent concentration, $C_{total}$, can be greater than in non-active (na)

tissue, resulting in variable amounts of contrast agent across the image. Defining the additional contrast agent concentration to occur within the interesting tissue, we can describe the total contrast agent concentration at locations (x,y) across the image as follows:

$$C_{total}(x,y)=C_{na}+\Delta C_{int}(x,y),$$

where $C_{na}$ is the concentration of the contrast agent in 'non-active' tissue, and is modelled as a constant value in all tissues, while an amount of additional contrast agent concentration in the interesting tissue, $\Delta C_{int}$, can vary at pixel locations, (x,y).

In the case of CE RI of non-active tissue, assuming equal contrast agent concentration in interesting and fatty tissues we have:

$$g_{CA}(x,y)_{na}=g_{fat\_CA}e^{-h_{int}(x,y)[\mu_{int}-\mu_f]}$$

Similar to the density estimation procedure in conventional mammographic images, a reference fat pixel value, but this time with a contrast agent (CA) present, "$g_{fat\_CA}$", can be found in 'non-active' adipose tissue, which gives:

$$g_{fat\_CA}=\lambda e^{-H(\mu_f+\mu/\rho_{CA}C_{na})}$$

where $\mu/\rho_{CA}$ is the mass attenuation coefficient of the contrast agent and the adipose tissue is assumed to be non-active in terms of additional contrast agent uptake. In one embodiment, the method of $g_{fat\_CA}$, point localisation follows the approach of PCT/GB2010/001472 except that the current approach is novel for taking into consideration effects of the contrast agent and insight into the effect of contrast agent in the LE RI versus the HE RI.

In the case of CE RI of a breast with active tissue, we observe an increased contrast agent attenuation relative to the fatty non-active reference, which can be described by:

$$g_{CA}(x,y)g_{fat\_CA}e^{-h_{int}(x,y)[\mu_{int}-\mu_f+\mu/\rho_{CA}\Delta C_{int}]}$$

The non-active fatty reference pixel values, $g_{fat\_CA}$, can be found in each of the LE and HE images as:

$$g_{fat\_CA\_LE}=\lambda_{LE}e^{-H(\mu_{f\_LE}+\mu/\rho_{CA\_LE}C_{na})}$$

$$g_{fat\_CA\_HE}=\lambda_{LE}e^{-H(\mu_{f\_HE}+\mu/\rho_{CA\_HE}C_{na})}$$

wherein the amount of tissue, H, and the contrast agent concentration in the nonactive tissue, $C_{na}$, are each assumed to be identical in the LE and HE views.

The equation for CE RI of a breast with active tissue, $g_{CA}(x,y)$, can similarly be expressed for each of the LE and HE images, including terms for the non-active fatty reference pixel values, as:

$$g_{CA\_LE}(x,y)=g_{fat\_CA\_LE}e^{-h_{int}(x,y)[\mu_{int\_LE}-\mu_{f\_LE}+\mu/\rho_{CA\_LE}\Delta C_{int}(x,y)]}$$

$$g_{CA\_HE}(x,y)=g_{fat\_CA\_HE}e^{-h_{int}(x,y)[\mu_{int\_HE}-\mu_{f\_HE}+\mu/\rho_{CA\_HE}\Delta C_{int}(x,y)]}$$

wherein the amount of interesting tissue, $h_{int}$ (x,y), and the additional contrast agent concentration, $\Delta C_{int}(x,y)$, are each assumed to be identical in the LE and HE views.

In LE images, the relative sensitivity to contrast agent concentration is low, such that the x-ray attenuation due to normal tissue overwhelms the measured image signal. For example, in typical clinical conditions, around 5% of the image signal, or less, might be attributed to the presence of an iodinated contrast agent. Thus, the relative difference between the added signal from a higher concentration of contrast agent in active tissue compared to the baseline non-active tissue contrast agent concentration is expected to be marginal.

Thus, minimal error is anticipated if we assume additional contrast agent concentration in interesting tissue is zero, $\Delta C_{int}(x,y)=0$, such that $g_{CA}(x,y) \approx g_{CA}(x,y)_{na}$ in the LE RI, and then solve for $h_{int}$ by re-arranging the above LE image equations to give:

$$h_{int}(x, y) = \log\left(\frac{g_{fat\_CA\_LE}}{g_{CA\_LE}(x, y)}\right)/(\mu_{int\_LE} - \mu_{f\_LE}).$$

This output, $h_{int}$ (x,y), represents an 'interesting tissue' thickness map, otherwise known as a density map, similar as described in PCT/GB2010/001472 except that the current approach is novel for taking into consideration effects of the contrast agent and insight into the effect of contrast agent in the LE RI versus the HE RI. In the above procedure, it is advantageous that, despite presence of contrast agent in the tissue in CE RI, knowledge of the non-active contrast agent concentration is not required to solve for the interesting tissue thickness $h_{int}(x,y)$. An example density map derived from the scatter-corrected LE image is shown in FIG. 2H where the greyscale represents the thickness of fibroglandular tissue.

To address many of the limitations in the prior art of measuring the contrast agent concentration from the recombined, or subtracted DE image, instead the relative increase in contrast agent concentration in interesting tissue, i.e. the additional contrast agent in interesting tissue $\Delta C_{int}(x,y)$, is calculated from the HE image the non-active fatty reference pixel values, $g$ $g_{fat\_CA\_HE}$, together with the thickness of interesting tissue $h_{int}$ (x,y). Rearranging the equation for the non-active fatty reference pixel values in the HE RI $g_{CA\_HE}$ (x,y) above, the additional contrast agent concentration in interesting tissue $\Delta C_{int}(x,y)$ can be solved for as:

$$\Delta C_{int}(x, y) = \frac{\dfrac{\log\left(\dfrac{g_{fat\_CA\_HE}}{g_{CA\_HE}(x, y)}\right)}{h_{int}(x, y)} - (\mu_{int\_HE} - \mu_{f\_HE})}{\mu/\rho_{CA\_HE}}.$$

An output, $\Delta C_{int}(x,y)$ is an additional contrast agent concentration in interesting tissue as determined from the HE RI and the LE RI. The output enables production of an additional contrast agent map in visible form of the locations of, and amount of increased contrast agent concentration in the breast, relative to the contrast agent concentration in fatty tissue, at locations where the thickness of interesting tissue $h_{int}$ (x,y)>0. It is the active tissue which preferentially takes up the contrast agent and so where the increased contrast agent concentration is present. Active tissue includes tumours which occur in regions of interesting tissue which includes fibroglandular tissue and lesions some of which may be tumours. Hence the limitation that $h_{int}$ (x,y)>0 is reasonable and not onerous for the purposes of accurately quantifying contrast agent in normal tissue and in cancerous tissue from CE RI and to assess and verify image quality and the efficacy of a clinical assessment from CE RI.

Figure 1:
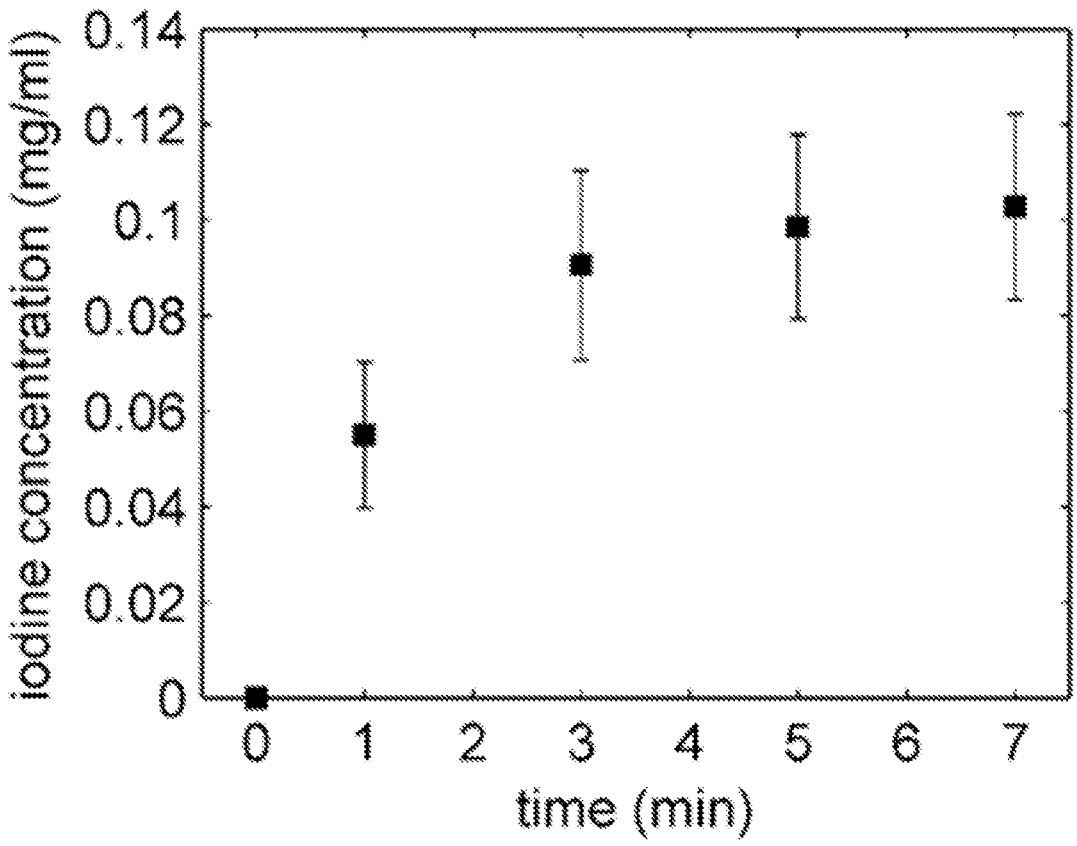
FIG. 1 shows iodine concentration in the normal tissue vs time after intravenous contrast agent administration estimated from measurements made on single-energy contrast-enhanced mammograms (Jong et al (2003))

In one embodiment, using additional model inputs that may include patient size, patient blood volume, patient heart rate, contrast agent injection rate, injection time relative to the CE RI image under analysis, breast compression, compression paddle type, and prior reference measurements such as from FIG. 1, a predictive estimate of the non-active contrast agent concentration could be made to permit estimation of the total contrast agent concentration, $C_{total}(x,y)$ However, due to the high uncertainty associated with many of these model inputs, it is an advantage of the method that an estimate of the amount and location of additional contrast agent concentration $\Delta C_{int}(x,y)$ can be made without knowledge of the contrast agent concentration in non-active tissue $C_{na}$. This improves image quality and clarity since any measurement or estimate of contrast agent concentration in non-active tissue $C_{na}$ would be inexact and introduce error and uncertainty.

Figure 3:
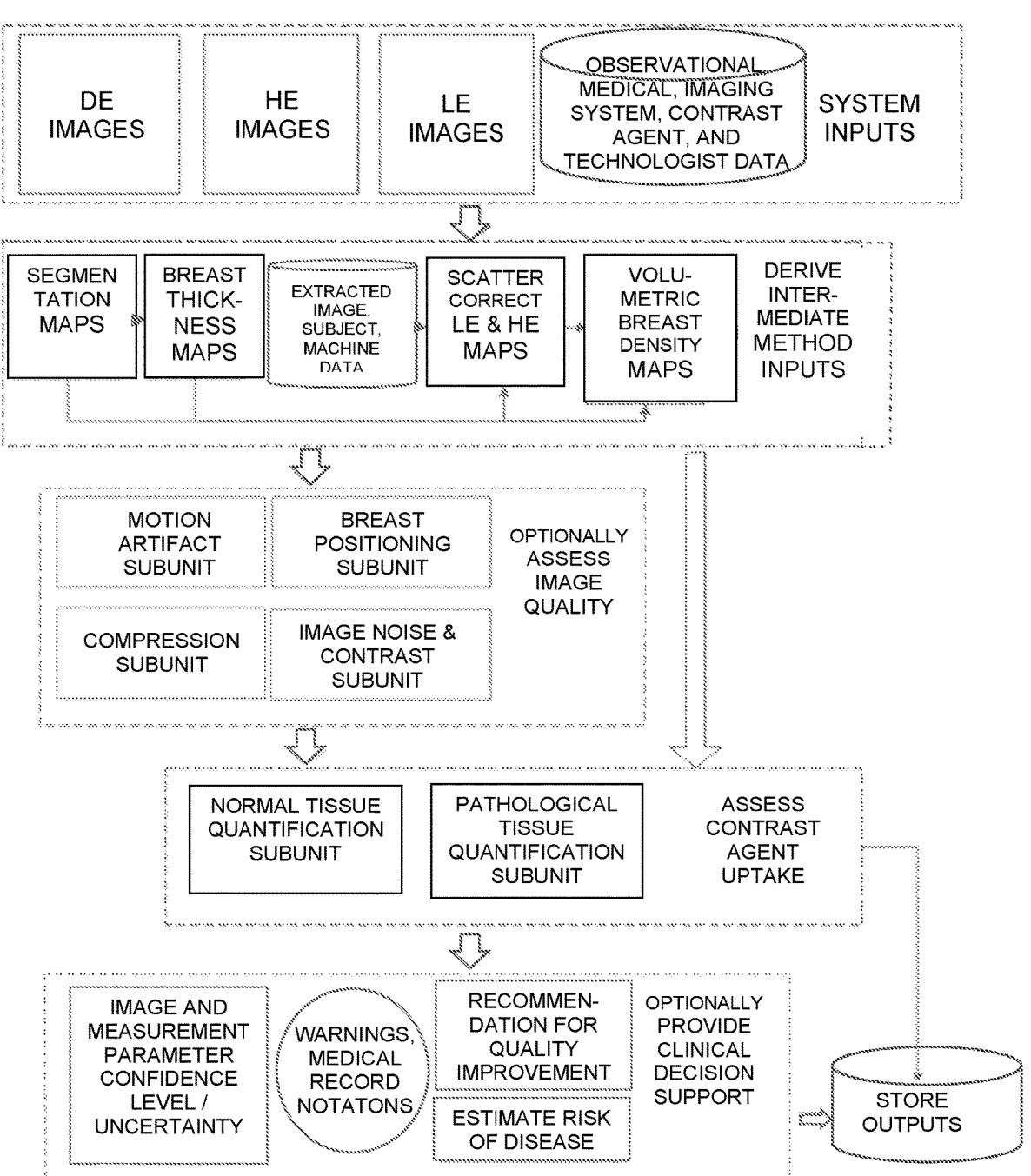
FIG. 3. shows an overall workflow of system and method for CE RI quantification, where steps of image quality assessment and clinical decision support are shown in optional groups because they are each optional steps that represent additional embodiments when combined with the central quantification method.

A flowchart of the main CE RI quantification system and method inputs and steps are shown in FIG. 3.

In one aspect, several measures can be derived from the output related to active tissue. For example, the additional contrast agent concentration map, $\Delta C_{int}(x,y)$, itself can be used directly as a visualisation of the increased contrast agent uptake in the interesting, or dense, tissue of the breast. Summary statistics about the marginal contrast agent concentration increase can be prepared, such as the average, standard deviation or maximum increased contrast agent concentration in dense tissue. These summary statistics may be used, alone or in a model to define quantifications and/or classifications of additional contrast agent concentration in interesting tissue $\Delta C_{int}(x,y)$ that correlate with BPE in an objective manner.

In a second aspect, measures of the pattern, or complexity of the additional contrast agent concentration in interesting tissue $\Delta C_{int}(x,y)$ distribution can be made. For example, by measurement of texture features of the additional contrast agent concentration map. The visual appearance of additional concentration in interesting tissue $\Delta C_{int}(x,y)$ is anticipated to correlate with BPE, and with the potential for masking of lesion contrast-enhancement by BPE. Thus, a CE RI-specific image quality measure related to potential masking by BPE can be determined. More clarity and less blur are both objectives.

In a third aspect, the additional contrast agent concentration in interesting tissue $\Delta C_{int}(x,y)$ map is analysed for information to either predict the presence of disease or characterise known diseased tissue. In one embodiment, manual contouring is used to define one or more regions of interest for quantitative evaluation, especially when disease is already suspected or confirmed. In a preferred embodiment the region(s) for analysis may be identified by automated means. For example, the additional contrast agent concentration in interesting tissue $\Delta C_{int}(x,y)$ map can be thresholded to localise areas of interest, or be used in combination with computer aided detection or machine-learned lesion localisation tools to indicate regions with suspicion of disease.

Figure 2K:
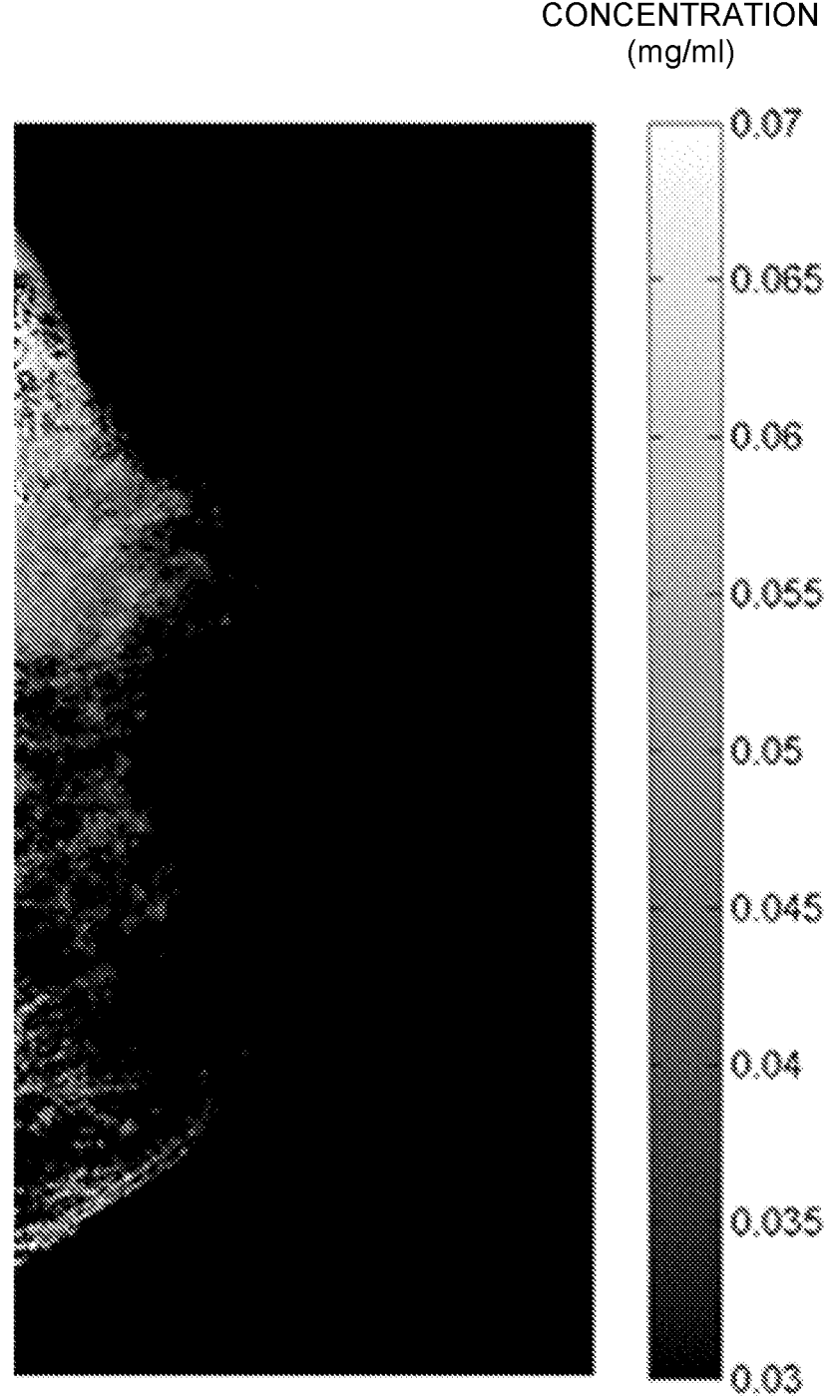
FIG. 2K is a additional contrast agent concentration in the interesting tissue map showing concentrations above a threshold level so as to threshold areas of maximum enhancement.

The resulting additional contrast agent concentration in interesting tissue $\Delta C_{int}(x,y)$ map from the quantification method applied to the illustrative CEDM case is shown in FIG. 2K. The additional contrast agent concentration in interesting tissue $\Delta C_{int}(x,y)$ map clarifies where there is active tissue such as tumour tissue which preferentially takes up the iodinated contrast agent compared to normal tissue. Good agreement of the increased iodine concentration observed in FIG. 2J is seen compared to that expected based on FIG. 1. FIG. 2J demonstrates that by thresholding the map, areas of maximum enhancement can be localised, which may indicate an area of disease.

In an embodiment, the accuracy of the additional contrast agent concentration of interesting tissue $\Delta C_{int}(x,y)$ estimate can be improved, for example by incorporation of contrast agent injection protocol information, such as the injected contrast agent volume and concentration, the injection start time relative to the image acquisition time, and patient factors, such as weight, estimated blood volume, and hormonal status. The use of these parameters, together with reference data on typical contrast agent tissue uptake also permits estimates of total contrast agent concentration, which will include the contrast agent content in the 'non-active' adipose tissue.

The result of DE image decomposition is effectively the HE image with a weighted proportion of the LE image signal removed, and the weighting selected to cancel the appearance of the normal tissue.

The normal tissue includes fibroglandular tissue which is non-active and fatty tissue. However, vendors may apply additional image corrections and processing, such as to compensate for tissue thickness variation and to maximize contrast enhancement. The image processing may interfere with quantitative interpretation, especially as different amounts of normal tissue suppression can be used in the DE images, which can result in substantially different visualisation of the tissue. The present invention entails a vendor neutral DE image that uses an optimal combination of the LE and HE images after motion compensation and scatter correction.

In an embodiment, a DE image weighting factor can be calculated as the ratio of the relative difference between the effective linear attenuation coefficients of the interesting and fatty tissue as:

$$w_{DE} = \frac{(\mu_{int} - \mu_f)_{HE}}{(\mu_{int} - \mu_f)_{LE}}.$$

The difference $\mu_{int}-\mu_f$ is indicative of the light:dark contrast between interesting tissue and fatty tissue. A DE image can then be produced from the motion-corrected and scatter-corrected LE and DE images by combining the images with the weighting factor, $w_{DE}$, as:

$$g_{DE}(x,y)=g_{HE}(x,y)-w_{DE}g_{LE}(x,y)$$

This DE image is referred to as a 'raw' DE image, as no processing for image enhancement has been applied. The 'raw' DE image shows the weighted 'raw' dual energy (DE) pixel values $g_{DE}(x,y)$. It is intended to clarify where there is active tissue.

Use of the raw DE image for diagnostic interpretation and quantitative CE RI analysis has the advantage that the data is vendor neutral and incorporates image corrections that minimize confounding factors for evaluation. It is anticipated that comparison of image quality measurements between the raw DE image and the vendor-supplied DE image will be useful to indicate potential image quality concerns, such as a difference in artefacts and masking potential between the images. Together with independent measures of the vendor-supplied DE image quality, the comparative analysis can be used to determine an overall score, or rating for the DE image quality. Image quality features of interest will include breast positioning, image noise, image contrast, presence of motion artefact, and measurements of the degree of normal tissue cancellation, based on measurements of 'anatomical noise' such as via power-law analysis and image texture. These latter measurements of anatomical noise will be included in a measurement and classification of BPE.

FIG. 2I is an example 'raw' DE image, computed using the scatter-corrected LE and DE images and the optimal DE image weighting factor calculated for this case.

This invention has been described by way of example only, modifications and alternatives will be apparent to those skilled in the art. All such embodiments and modifications are intended to fall within the scope of the present invention.

The invention claimed is:

1. A method of contrast-enhanced radiographic image processing to assess uptake of a radio-opaque contrast agent in organ tissue in a patient including an adipose tissue and interesting tissues, wherein non-active tissues include the adipose tissue and a fibroglandular non-active tissue, active tissues include lesions and a fibroglandular active tissue, and the interesting tissues include the active tissues and a portion of the non-active tissues, wherein the method comprises:

administering the radio-opaque contrast agent to the patient;

taking low energy (LE) and high energy (HE) radiographic images (RI) of the organ tissue;

quantifying the radio-opaque contrast agent only where the interesting tissues have a thickness greater than zero, the interesting tissues including fibroglandular tissue and any lesions of the organ tissue;

adopting a relation that a total concentration of the radio-opaque contrast agent in the active tissues is a sum of a concentration of the radio-opaque contrast agent in the non-active tissues plus an additional concentration of the radio-opaque contrast agent only in the interesting tissues according to location in the HE RI; and determining the thickness of the interesting tissues by an adopting a relation that in the LE RI there is no difference between the total concentration of the radio-opaque contrast agent in the active tissues versus in the non-active tissues.

2. The method according to claim 1 including a step of x-ray scatter correction of the LE RI and HE RI.

3. The method according to claim 1 including producing a thickness map(s) of the organ tissue using the LE RI to determine a volumetric composition map.

4. The method according to claim 1 including determining the additional concentration of the radio-opaque contrast agent only where the interesting tissues have a thickness greater than zero.

5. The method according to claim 1 including adopting a relation that additional concentration of the radio-opaque contrast agent relative to the radio-opaque contrast agent in adipose material occurs only in the interesting tissues, the interesting tissues including fibroglandular tissue and any lesions of the organ tissue.

6. The method according to claim 1 including adopting a relation that the concentration of the radio-opaque contrast agent in the non-active tissues is less than that of the total concentration of the radio-opaque contrast agent in the active-tissues.

7. The method according to claim 4 including determining an objective measure by correlating the additional concentration of the radio-opaque contrast agent only in the interesting tissues, but excluding the lesions, with a benign parenchymal enhancement.

8. The method according to claim 1 including an assessment of quality of the LE and HE RI wherein an estimate of an uncertainty in the additional concentration of the radio-opaque contrast agent only in the interesting tissues is made.

9. The method according to claim 1 wherein image corrections are made to the LE RI and the HE RI according to image quality assessment and are used to produce a Dual Energy (DE) RI, wherein a weighting factor is determined from a first difference between a linear attenuation coefficient of the interesting tissues and the adipose tissue in the HE RI, and a second difference between the linear attenuation coefficient of the interesting tissues and the adipose tissue in the LE RI and determining the ratio of the first difference to the second difference.

10. The method according to claim 1, including producing a map in visual form of the additional concentration of the radio-opaque contrast agent in the interesting tissues according to location in the HE RI.

11. A radiographic image processing system on a non-transitory computer-readable medium and executable to implement the method according to claim 1.

\* \* \* \* \*